United States Patent [19]

Horrobin

[11] Patent Number: 5,422,115
[45] Date of Patent: Jun. 6, 1995

[54] METHODS OF TREATMENT AND DEVICES EMPLOYING LITHIUM SALTS

[75] Inventor: David F. Horrobin, Haslemere, United Kingdom

[73] Assignee: Efamol Holding PLC, Surrey, United Kingdom

[21] Appl. No.: 963,597

[22] Filed: Oct. 20, 1992

Related U.S. Application Data

[60] Division of Ser. No. 329,881, Mar. 28, 1989, abandoned, which is a continuation of Ser. No. 182,291, Apr. 15, 1988, abandoned.

[30] Foreign Application Priority Data

Apr. 27, 1987 [GB] United Kingdom ............... 8709892
Aug. 25, 1987 [GB] United Kingdom ............... 8719988
Jan. 29, 1988 [GB] United Kingdom ............... 8802016

[51] Int. Cl.$^6$ .................... A61K 9/28; A61K 31/20
[52] U.S. Cl. .................... 424/422; 424/474; 424/475; 424/480; 424/482; 424/423; 424/436; 514/810; 514/821; 514/866; 514/886; 514/825; 514/885; 514/824; 514/931; 514/934

[58] Field of Search ............... 424/464, 465, 474, 475, 424/480, 482, 422; 514/558

[56] References Cited

U.S. PATENT DOCUMENTS 4,753,964 6/1988 Horrobin .......................... 514/558

Primary Examiner—Thurman K. Page
Assistant Examiner—James M. Spear
Attorney, Agent, or Firm—Foley & Lardner

[57] ABSTRACT

Methods of treatment of the human or animal body are provided to combat conditions responsive to lithium and/or $C_{18-22}$ polyunsaturated fatty acid therapy, including conditions associated with essential lithium deficiency, and also transfer of lipid-enveloped viruses between humans or animals or between cells within a human or animal body. The methods include administration of an effective amount of a lithium salt of a $C_{18-22}$ polyunsaturated fatty acid. Devices for combatting transmission of viral diseases including lithium salts of a $C_{18-22}$ polyunsaturated fatty acid are also provided.

15 Claims, No Drawings

METHODS OF TREATMENT AND DEVICES EMPLOYING LITHIUM SALTS

This application is a division of application Ser. No. 07/329,881, filed Mar. 28, 1989, which in turn is a continuation of Ser. No. 07/182,291, filed Apr. 15, 1988, both now abandoned.

The present invention relates to pharmaceutical, nutritional and disinfectant compositions, in particular to such compositions containing lithium salts of polyunsaturated fatty acids, to the use of such lithium salts in the preparation of pharmaceutical compositions and to therapeutic treatments of the human or non-human body with such lithium salts.

The oral and parenteral administration of lithium salts, in particular salts such as lithium carbonate, has found widespread use in the treatment of manic depressive psychosis. Oral administration of lithium salts conjointly with polyunsaturated fatty acids such as dihomo-gamma-linolenic acid, gamma-linolenic acid and linoleic acid has also been suggested for use in the treatment of Alzheimer's disease and inflammation and smooth muscle spasm arising from imbalances in the body's prostaglandin levels. Lithium salts have also been used successfully for the topical treatment of viral infections such as genital herpes.

Lithium salt therapy has also been used in or proposed for the treatment of several other conditions, such as for example alcoholism, various dementias, aggression, schizophrenia, unipolar depression, skin disorders (including contact dermatitis, atopic dermatitis, seborrhoeic dermatitis, psoriasis and acne), immunological disorders, asthma, multiple sclerosis, rheumatoid arthritis, Crohn's disease, ulcerative colitis, and irritable bowel syndrome.

Polyunsaturated fatty acids are also known to possess physiological activities, including virucidal activities, and have been used in or proposed for the treatment of conditions such as for example atopic disorders (including eczema, asthma and allergic rhinitis), disorders associated with atopy, (including Crohn's disease, ulcerative colitis, otitis media and nephrotic syndrome), benign diseases of the breast and prostate glands, premenstrual breast disease (cyclical mastalgia), breast, prostatic or other cancers, diabetes and the complications of diabetes (including nephropathy, neuropathy, retinopathy and microvascular and macrovascular cardiovascular complications), alcoholism and the complications of alcoholism, psychiatric disorders including schizophrenia, depression and tardive dyskinesia, conditions associated with elevated blood cholesterol and/or triglyceride levels, with elevated blood pressure, with an increased risk of development of thrombotic disorders, with an increased risk of development of coronary heart diseases, with ulcers in the stomach, duodenum or any other part of the gastrointestinal tract, with reflux oesophagitis or irritable bowel syndrome, and with rheumatoid arthritis, osteoarthritis or other diseases associated with inflammation, damage to connective tissue or disordered immune function such as Sjogren's syndrome, Raynaud's syndrome, systemic lupus erythematosus, polyarteritis nodosa, primary biliary cirrhosis, and multiple sclerosis, diseases of the kidneys including acute and chronic glomerulonephritis, nephrotic syndrome, diabetic nephropathy, and disorders associated with immunosuppression caused by cyclosporin or other immunosuppressive agents. Polyunsaturated fatty acids are also used in enteral and parenteral alimentation, e.g. of patients who are to be or have been subjected to surgery. In parenteral alimentation or nutrition however it has not proved-to be simple to formulate a single parenterally administrable composition capable of meeting the patient's entire nutritional requirements as although the majority of essential nutrients, e.g. vitamins, minerals and calorie sources, may be formulated in aqueous solution the essential fatty acids, due to their lipid nature, can not.

The difficulties associated with the preparation and administration of homogeneous single phase parenteral nutrition solutions have thus been such that the essential fatty acids have commonly been omitted from such solutions. Consequently where parenteral nutrition has had to be performed over a period so prolonged that omission of the essential fatty acids could not be tolerated it has been necessary to administer the essential fatty acids separately, as lipid emulsions, and in practice problems have been encountered and dangers (e.g. of fat embolism) have been foreseen with such parenteral administration of lipid emulsions, especially to infants.

Thus, solutions for long term parenteral nutrition typically contain ingredients such as essential amino acids, proteins, glucose and/or other carbohydrates, sodium, potassium, calcium, magnesium, chloride, acetate, phosphate, zinc, copper, iodine, manganese, vitamins A, D, E, C, $B_1$, $B_2$, $B_6$, $B_3$, pantothenic acid and folic acid. Other essential micronutrients may also be added. Thus for example a parenteral nutrition solution might typically contain alanine, arginine, aspartic acid, cysteine and/or cystine, glutamic acid, glycine, histidine, isoleucine, leucine, lysine, L-methionine, phenylalanine, proline, serine, threonine, tryptophan, tyrosine, valine, dextrose, sodium, potassium, calcium, chloride and magnesium and might have added thereto, before administration, further minerals, e.g. sources for phosphate, copper, iron, manganese, zinc, fluoride, and iodide. Such a parenteral nutrition solution can be made up for example from Vamin Glucose and Ped-El (both available from KabiVitrum Ltd. of Uxbridge, United Kingdom).

Solutions for short term intravenous fluid and nutrition support around the times of surgical or other procedures which may temporarily Prevent oral nutrition typically include glucose in some form of physiologically acceptable saline or buffer solution.

Neither the short or long term types of parenteral nutrition solution contain essential fatty acids even though where the patient is receiving only parenteral alimentation essential fatty acid deficiency may develop rapidly for at least three reasons: (1) no essential fatty acids are being taken in orally, (2) the parenteral solutions tend to block mobilization of lipids from body stores, so reducing the ability to make use of the body's own content of essential fatty acids, and (3) the high glucose intake in particular tends to inhibit 6-desaturation of the essential fatty acids linoleic acid and alpha-linolenic acid. 6-desaturation within the body is required if these essential fatty acids are to exert their full nutritional effects.

As mentioned above, essential fatty acids must normally be administered in the form of lipid emulsions, usually containing linoleic acid with or without alpha-linolenic acid. Some specialist emulsions, especially for use in paediatrics, may also contain 6-desaturated fatty acids such as the n-6 essential fatty acid gamma-linolenic acid and the n-3 essential fatty acid eicosapentaenoic acid. Such emulsions are not free of side effects and there is particular concern about their effects on the lungs of premature infants. Typical essential fatty acid emulsions for parenteral nutrition are for example the Intralipid products of KabiVitrum Ltd.

As mentioned above, conjoint administration of lithium salts and of polyunsaturated fatty acids has been proposed for the treatment of disorders believed to be associated with prostaglandin imbalance and in EP-A-234733 orally administrable capsules containing lithium gammalinolenate and/or lithium eicosapentaenoate for use in the treatment of Alzheimer's disease are proposed. There has however been no suggestion that any particular benefit in terms either of drug delivery or of therapeutic efficacy might arise from the use of lithium-polyunsaturated fatty acid salts and indeed there has been no suggestion that administration of such salts may have any therapeutic effect beyond that expected for conjoint administration of a lithium salt and of a polyunsaturated fatty acid. Furthermore, as discussed below, the major benefit of such use is not achieved on oral administration unless the salts are administered in a manner which delays release until after the stomach is passed.

We have now found that the lithium salts of polyunsaturated fatty acids have surprisingly beneficial physicochemical properties which make them particularly suitable compounds for use in the administration of lithium in lithium therapy or for the administration of polyunsaturated fatty acids in polyunsaturated fatty acid therapy.

In particular we have found that, while most physiologically tolerable lithium salts are not readily lipid soluble and most polyunsaturated fatty acids are not readily water-soluble, lithium salts of polyunsaturated fatty acids surprisingly are crystalline solids at ambient temperature which are highly soluble in both water and alcohol. Consequently these properties particularly facilitate preparation of pharmaceutical and other compositions using the salts and the salts may be used to promote lithium and/or polyunsaturated fatty acid uptake following administration, especially where movement of lithium and/or polyunsaturated fatty acid from an aqueous phase to a lipid phase or vice versa may be desirable. Thus, for example, the lithium salts conventionally used in lithium therapy (which, as mentioned above, are not readily lipid soluble) may have difficulty entering primarily lipid environments so presenting problems where such entry (e.g. penetration into cells, into the skin or across the blood-brain barrier) is desirable, whereas entry of lithium into such lipid environments will be facilitated for lithium salts of the polyunsaturated fatty acids.

Equally, the relatively poor water solubility of the conventionally administered polyunsaturated fatty acids presents problems when attempting to ensure an even distribution of the fatty acid through both the intravascular and extravascular compartments of the extracellular fluid or when attempting to administer polyunsaturated fatty acids enterally (especially in patients with lipid malabsorption) or parenterally, and particular intravenously, or when administering polyunsaturated fatty acids, topically in a cosmetically acceptable aqueous base, and these problems may be reduced by administering the acid as its water-soluble lithium salt.

Thus viewed from one aspect the invention provides a pharmaceutical composition comprising a lithium salt of a $C_{18-22}$ polyunsaturated fatty acid having at least two unsaturated carbon-carbon bonds (said salt being referred to hereinafter as a Li($C_{18-22}$PUFA) salt) together with at least one physiologically acceptable excipient or carrier material, with the proviso that where said composition is in a solid form adapted for oral administration into the stomach in the treatment of Alzheimer's disease said lithium salt therein is provided with a gastric juice resistant release delaying coating. Preferred compositions include compositions for combatting enveloped viruses and diseases associated therewith and for combatting conditions responsive to lithium and/or $C_{18-22}$PUFA therapy.

Viewed from a further aspect the invention also provides the use of a Li($C_{18-22}$PUFA) for the manufacture of a therapeutic agent for the treatment of conditions responsive to lithium and/or $C_{18-22}$PUFA therapy with the proviso that where the agent is to be in a solid form adapted for oral administration into the stomach in the treatment of Alzheimer's disease the Li($C_{18-22}$PUFA) salt therein is provided with a gastric juice resistant release delaying coating. The conditions in the treatment of which the therapeutic agent may be used thus include the various conditions mentioned herein as being ones for which lithium and/or $C_{18-22}$ PUFA therapy has been suggested. Particularly preferably however the therapeutic agent may be used in parenteral nutrition or in the treatment of conditions selected from: essential fatty acid deficiency and conditions associated therewith; inflammatory and immunological disorders (including rheumatoid arthritis, osteoarthritis, atopic dermatitis and other forms of dermatitis, psoriasis, Crohn's disease and ulcerative colitis); psychiatric disorders (including manic-depressive psychosis, schizophrenia and alcoholism); disorders associated with smooth muscle spasm (including asthma, ulcerative colitis and dysmenorrhoea); diabetes and the renal, neurological retinal and cardiovascular complications of diabetes; cancers (including breast, prostatic and other cancers); and cardiovascular disorders (including elevated blood pressure, elevated blood levels of triglycerides, of total cholesterol or of LDL cholesterol, and thrombotic disorders).

Li($C_{18-22}$PUFA)s may also advantageously be used to inhibit transfer of enveloped viruses both between surfaces outside the body and between cells within the body and thus viewed from a still further aspect the invention also provides a disinfectant composition, for example for surface cleansing, e.g. cleansing of inanimate surfaces prone to vital contamination, comprising a Li($C_{18-22}$PUFA) together with at least one carrier material, and optionally together with a further biocidal agent, e.g. a virucide or a bactericide.

Viewed from a yet still further aspect the invention also provides a method of treatment of the human or animal body to combat conditions responsive to lithium and/or $C_{18-22}$ PUFA therapy, said method comprising administering to said body an effective amount of a Li($C_{18-22}$PUFA), with the proviso that where the Li($C_{18-22}$PUFA) salt is administered orally into the stomach for the treatment of Alzheimer's disease it is provided with a gastric juice resistant coating.

When administered orally into the stomach, due to the pH of the stomach contents, Li($C_{18-22}$PUFA) salts are liable to dissociate so reducing the effect of the lithium and PUFA entities of enhancing each other's transferability across aqueous/lipid phase boundaries and thus for oral administration according to the invention the Li($C_{18-22}$PUFA) salt is most preferably presented in a manner adapted to minimize dissociation in the stomach, e.g. by provision with an enteric, i.e. gastric juice resistant, coating or casing or by administration by tube, e.g. as a solution, directly into the intestines. Suitable enteric coated compositions thus include capsules or tablets provided with an enteric coating of an acrylate (such as the enteric Eudragit coating materials produced by Röhm GmbH), cellulose acetate phthalate or other appropriate material which serves to delay active substance release until the composition reaches the intestines.

Lithium therapy has hitherto been performed under a constraint arising from the toxicity of lithium. However where the therapy requires transfer of lithium into or through a lipid phase, e.g. through cell walls or across the blood-brain barrier, using Li($C_{18-22}$ PUFA)s it may be possible to deliver lithium ions to particular sites at concentrations previously attainable only at unacceptably toxic lithium dosages.

Thus, for example, in antiviral therapy as the $C_{18-22}$ PUFAs are themselves known to possess virucidal activities, the $C_{18-22}$ PUFA counterion not only will serve to target the virucidal lithium ions on lipid-rich environments thus enabling localized build up of lithium ions at concentrations otherwise achievable only at unacceptably toxic lithium dosage levels but it will also contribute to the overall virucidal efficacy of the composition.

The Li($C_{18-22}$ PUFA) in the compositions of the invention is preferably the salt of an acid which has 2–6 carbon-carbon double bonds and suitable Li($C_{18-22}$ PUFA)s include the lithium salts of linoleic acid, alpha-linolenic acid, gamma-linolenic acid, dihomo-gamma-linolenic acid, arachidonic acid, adrenic acid, 22:5n-6, 18:4n-3, 20:4n-3, eicosapentaenoic acid, 22:5n-3, docosahexaenoic (22:6n-3) acid, and mixtures of two or more such salts. Lithium salts of n-3 and n-6 $C_{18-22}$ PUFAs, especially 6-desaturated PUFAs are particularly preferred and where the pharmaceutical compositions of the invention are for use as nutritional compositions or as nutritional supplements, it is preferred that they contain at least one lithium salt of a $C_{18-22}$ PUFA in the n-3 series (e.g. 18:3n-3 (alpha linolenic acid), 18:4 n-3, 20:4 n-3, 20:5n-3, 22:5 n-3 and 22:6n3) and at least one lithium salt of a $C_{18-22}$ PUFA in the n-6 series (e.g. 18:2 n-6 (linolenic acid), 18:3n-6 (gamma-linolenic acid), 20:3n-6 (dihomogamma-linolenic acid), 20:4n-6 (arachidonic acid), 22:4n-6 (adrenic acid) and 22:5n-6). Lithium gamma-linolenate, which is a white solid at ambient temperature and is soluble in water and in alcohol in amounts in excess of 3 g/100 ml is especially preferred.

To optimize the targeting of the lithium ions onto lipid-rich sites, the compositions of the invention intended for use in lithium therapy preferably contain no further lithium salts than the Li($C_{18-22}$ PUFA); there may however be conditions in the treatment of which it is desirable to present lithium both as a lipid soluble salt and as a primarily water-soluble salt.

The nature of the carrier material or excipient in the compositions of the invention will of course depend on the end use to which the composition is to be put.

The compositions of the invention may conveniently comprise the Li($C_{18-22}$PUFA) incorporated into a solid, liquid or aqueous carrier medium and the pharmaceutical compositions may be in forms suitable for topical, enteral, oral, rectal, vaginal, or parenteral (e.g. intravenous, subcutaneous, intramuscular or intravascular) administration to the human or animal body. The compositions, methods and uses of the present invention are however especially suited to the oral, parenteral and topical and especially oral and intravenous, administration of Li($C_{18-22}$PUFA) salts. The pharmaceutical and disinfectant compositions are particularly suited respectively for oral or parenteral administration or for the topical treatment of inanimate surfaces or materials, such as kitchen, bathroom, toilet or surgery surfaces or surgical or dental equipment.

For the treatment of inanimate surfaces, the disinfectant compositions of the invention particularly preferably have as a carrier a substrate web impregnated with the Li($C_{18-22}$ PUFA). Thus, the disinfectant compositions of the invention may for example comprise a liquid or powder disinfectant base incorporating the Li($C_{18-22}$ PUFA), optionally together with further biocidal, e.g. virucidal, and/or lipophilic components, optionally carried by a web substrate. The pharmaceutical compositions of the invention may also if desired be incorporated into a web substrate. Thus a pharmaceutical composition may advantageously comprise a dressing with impregnated therein a Li($C_{18-22}$ PUFA) salt. Such dressings may be used for application to skin lesions with or without occlusion.

Where the composition of the invention comprises a web substrate, such as for example a cellulosic tissue or a woven or non-woven absorbent web, the substrate may be wet or dry according to the desired end use.

For external topical application to human or animal tissue, or for anal or vaginal application, the compositions of the present invention will generally be in the form of gels, creams, ointments, sprays, soaps, lotions, shampoo, emulsions or douches, or other cosmetic or skin or hair care formulations, and the compositions may particularly suitably contain as a carrier a further lipophilic component, e.g. a lipid or a lipid solvent, to enhance the lipid targetting property of the composition. The Li($C_{18-22}$PUFA) salts are likely to prove particularly valuable for application to the skin because of the rich lipid content of the skin and the need for agents acting on the skin to move easily from lipid to aqueous phases and vice versa. These water soluble Li($C_{18-22}$PUFA) salts thus enable essential fatty acids to be delivered to the skin in compositions which are particularly cosmetically acceptable and do not feel unduly greasy or oily.

As the optional further lipophilic component for the compositions of the invention, particular mention may be made of the polyunsaturated fatty alcohols, especially the alcohol analogues of the $C_{18-22}$ PUFAs. These alcohols are especially preferred as carriers in the compositions of the invention, not only because of the solubility within them of the Li($C_{18-22}$ PUFA) s but also because they themselves are powerful anti-viral agents.

Other suitable lipophilic components include free polyunsaturated fatty acids (e.g. $C_{18-22}$ PUFAs) or other derivatives thereof, such as esters (e.g. $C_{1-4}$ alkyl esters such as ethyl esters), amides and glycerides (e.g. mono-, di- and tri-glycerides). Particularly suitable as triglycerides are those derived from evening primrose oil, an oil containing gamma-linolenic acid and linoleic acid. Other vegetable oils which may be used as the source for suitable $C_{18-22}$ PUFAs or their derivatives include cotton seed, soybean, peanut, corn, safflower, sunflower seed, poppy seed, linseed, perilla, blackcurrant seed and borage seed oils. Fish oils may also be used.

For oral or rectal administration, the pharmaceutical compositions of the invention may be formulated using conventional pharmaceutical carriers and excipients, e.g. in the form of tablets, coated tablets, syrups, suppositories, capsules, powders, suspensions, emulsions, sprays, etc. As discussed above, since the Li($C_{18-22}$PUFA) salts may dissociate at the normal pH of the stomach contents (but not at the pH of intestinal contents or of other body fluids), oral administration forms will particularly preferably have the Li($C_{18-22}$PUFA) provided with an enteric coating to delay release of the Li($C_{18-22}$ PUFA) until it has passed through the stomach. Thus enteric coated capsules or tablets are especially preferred. Solutions or suspensions for administration by enteral tube or for rectal administration are also preferred.

For injection, the pharmaceutical compositions of the invention are preferably formulated as sterile solutions, emulsions or suspensions, e.g. in water for injections, or in solutions in a lipid or lipid solvent, again preferably also including further lipophilic and/or virucidal components. To enhance further the targeting of the compositions onto lipid-rich zones of the body, the Li($C_{18-22}$ PUFA) salts may optionally have a carrier in liposome, artificial chylomicron or micelle form.

The pharmaceutical compositions of the invention in parenterally administrable form may be used with particular advantage in parenteral alimentation. Thus parenterally administered Li($C_{18-22}$PUFA)s may be used as a means of supplying the essential fatty acids in parenteral alimentation or to prevent or treat essential fatty acid deficiency. Accordingly pharmaceutical compositions according to the invention may be administered to patients receiving total parenteral nutrition for short or long periods either as a source of essential fatty acids or as complete nutrition compositions. As discussed above, the essential fatty acids, which are essential nutrients, can at present only be administered in the form of lipid emulsions which are not always convenient or satisfactory. The lithium salts of the essential fatty acids, such as lithium linoleate, lithium gamma-linolenate, lithium eicosapentaenoate, etc, can however be readily administered in aqueous solutions. They could be incorporated into aqueous solutions for parenteral nutrition at the time of manufacture or, alternatively, could be made up into sterile vials to be added to intravenous fluids at, the time of setting up intravenous infusions. Consequently, in one particularly preferred embodiment, the pharmaceutical composition of the invention is in the form of a parenteral nutrition composition comprising at least one lithium salt of a n-3 $C_{18-22}$ polyunsaturated fatty acid and at least one lithium salt of a n-6 $C_{18-22}$ polyunsaturated fatty acid, preferably a composition comprising in aqueous solution said Li($C_{18-22}$ PUFA) salts and at least one further nutritional component selected from: vitamins, essential minerals and calorie sources.

It is usually stated that about 1% of daily kilocalorie intake should be in the form of essential fatty acids, though in special circumstances as much as 5% might be needed. An adult, resting in bed, and requiring a daily intake of 2000 kilocalories might therefore need 20 to 100 kilocalories in the form of essential fatty acids. Since lipids provide about 9 kcal/g, the essential fatty acid requirement could be fulfilled by 2-11 g per day of lithium salts of essential fatty acids providing a daily intake in the region of 50 to 250 mg of lithium. The daily intake of lithium in someone receiving 1500 mg of lithium carbonate orally per day for the treatment of manic depression is 270 mg and so in most situations there should be a wide margin of safety in the daily lithium dose when essential fatty acids are given parenterally as lithium salts. Since lithium has been shown to stimulate the production of white blood cells, especially in situations where their levels are depressed by radiation or chemotherapy for malignant tumours, the administration of Li($C_{18-22}$ PUFA) salts in this way could have other desirable effects.

The compositions of the invention, in sterile solution suspension or emulsion form, may also if desired be used for wound irrigation, e.g. during surgery where there is a risk of transfer of vital infection.

In the case of compositions for the treatment of inanimate surfaces, after application the compositions according to the invention may be removed or they may be left, e.g. as a prophylactic coating. Thus for example compositions according to the invention may be applied to condoms or other sexual devices and viewed from another aspect the invention provides sexual appliances, such as barrier contraceptives, e.g. condoms, film and spray contraceptives, provided with a coating of or impregnated with a virucidal composition according to the invention, whereby to reduce the risk of sexual transmission of vital infection. In such cases, the carrier for the Li($C_{18-22}$ PUFA) is particularly suitably a cream, gel, oil or emulsion.

Viewed from a yet further aspect, the present invention provides a process for the preparation of a composition according to the invention, said process comprising obtaining a Li($C_{18-22}$ PUFA) salt and subsequently incorporating said salt into at least one sterile excipient or carrier material, preferably including a $C_{18-22}$ polyunsaturated fatty alcohol, or an ester, amide or glyceride of a $C_{18-22}$ polyunsaturated fatty acid.

Besides their utility in conventional lithium and $C_{18-22}$PUFA therapies, the compositions of the present invention are generally suitable for use in combatting or inactivating lipid-enveloped viruses, such as for example herpetic, pox and wart viruses and other viruses producing pathological effects on the skin, and especially sexually transmittable viruses, including viruses transmitting acquired immune deficiency syndrome.

Thus, viewed from a further aspect, the invention provides a method of combatting transfer of lipid-enveloped viruses comprising the surface application of, or the therapeutic or prophylactic treatment of a human or animal body with, a Li($C_{18-22}$ PUFA), preferably by application of a virucidal composition according to the invention or a sexual appliance according to the present invention. In one particularly preferred embodiment, the method of the invention is a method of inhibiting the transmission of sexually transmitted diseases associated with lipid-enveloped viruses, said method comprising applying a composition or appliance according to the invention to inanimate or external body surfaces susceptible to contact with body fluids.

Viewed from a yet further aspect, the invention also provides the use of a Li($C_{18-22}$ PUFA) for the manufacture of a therapeutic or prophylactic agent or device for use in a method of combatting lipid-enveloped viruses, and especially a method of inhibiting transmission of such viruses between humans or animals or between cells in the human or animal body.

The concentration of the Li($C_{18-22}$ PUFA) in the compositions of the invention will of course depend upon the physical nature of the composition as well as on its desired end use. However, for compositions for application or administration to the human body the concentration may conveniently be such that each day or on each application or administration the body receives 1 mg to 100 g of the Li($C_{18-22}$ PUFA), preferably 100 mg to 10 g, most preferably 200 mg to 1 g.

In the case of orally or parenterally administrable compositions, the compositions are preferably administered at a daily or one-off dosage of the Li($C_{18-22}$ PUFA) of 1 to 100,000 mg, especially 1-50000 mg, preferably 100-10000 mg, conveniently in dosage units of 50, 100, 250, 500 or 1000 mg. For topical administration, Li($C_{18-22}$ PUFA) concentrations by weight of 0.001 to 50%, for example from 0.01 to 30%, preferably 0.1 to 5%, may be appropriate.

As mentioned above lithium has long been known to have various therapeutic effects in the treatment of certain diseases and ailments. Nonetheless lithium treatment has often been accompanied by a number of side effects related to dosage and degree of accumulation and medical texts have advised that lithium should be administered under close medical supervision. It was thus with surprise that we found that significantly depressed lithium plasma levels, relative to those of healthy subjects, are associated with a number of ailments and diseases, in other words that lithium appears to be an essential trace element.

Thus in healthy subjects lithium plasma levels may generally be in excess of 0.04 mM/l, whereas in subjects suffering from atopic eczema or seborrheic dermatitis mean plasma levels of below 0.025 mM/l are found. Alcoholics, patients with psoriasis, candidiasis, pityriasis and other fungal skin infections and sufferers from combination skin similarly exhibit depressed lithium plasma levels. Combination skin is a troublesome and unsightly complaint manifested by excessive greasiness in certain skin areas, such as the forehead and the nose, and excessive dryness in other skin areas, such as the sides of the face).

In our copending British Patent Application No. 8719985, filed 25 Aug. 1987 (a copy of which is on the Patent Office file of the present application) whose disclosures are incorporated herein by reference, lithium containing nutritional supplements for combatting conditions associated with essential chemical deficiency are described. For such supplements, which for the purposes of the claims of the present application are regarded as pharmaceutical compositions, it will be highly advantageous to incorporate the lithium in the form of its salt with a $C_{18-22}$ polyunsaturated fatty acid, especially where the supplement is in the form of a topically administrable composition, e.g. a cream, gel or ointment, a parenterally administrable composition, e.g. an aqueous solution, or an orally administrable composition, e.g. tablets or capsules and, particularly, orally administrable compositions in which the lithium salt is provided with a gastric juice resistant release delaying coating. Thus in one preferred embodiment of the invention the pharmaceutical composition of the invention takes the form of a nutritional supplement.

Such nutritional supplements, which most preferably are sterile, may be in a form adapted for enteral, parenteral or topical administration, but most preferably will be in a form adapted for oral ingestion. Liquid preparations made with sterile or deionized water are particularly preferred. However, in another preferred embodiment the nutritional supplement may take the form of dietary supplement, such as a foodstuff. The nutritional supplement may alternatively be in a conventional pharmaceutical dosage form adapted for administration to the gastrointestinal tract.

In this regard, forms such as tablets, coated tablets, capsules, powders, drops, suspensions, solutions, syrups and suppositories deserve particular mention. Nevertheless as lithium nutritional supplementation may be achieved by parenteral or topical administration, for example by injection or by topical application (e.g. of an ointment, lotion, cream, paste or gel or the like), or by transdermal iontophoretic delivery, the nutritional supplement may be in the form of a composition adapted for one of these administration modes.

Where the nutritional supplement is prepared in a conventional pharmaceutical dosage form it may of course also contain conventional pharmaceutical carriers or excipients.

For oral administration, the nutritional supplement may conveniently take the form of a foodstuff, for example a food or drink mix, into which a Li($C_{18-22}$ PUFA) salt is incorporated. The nutritional supplement may particularly suitably be in the form of a so-called "complete" foodstuff, analogous to those which are prepared to serve as the major or sole source of nutrition for example for people wishing to loose weight, for post-operative patients, for elderly patients, for convalescents, or for individuals with specific dietary needs (e.g. patients with diabetes, coeliac disease or cystic fibrosis). For most people however a lithium supplemented foodstuff will preferably be of a type that is ingested daily in similar quantities, and for this reason the supplement will particularly conveniently comprise the Li($C_{18-22}$ PUFA) salt and a cereal or legume foodstuffs base. In an especially preferred embodiment, the nutritional supplement may be in the form of a breakfast cereal. In a preferred alternative, however, the nutritional supplement may take the form of a lithium-containing multi-vitamin/multi-mineral preparation, for example in the form of tablets, capsules, or drops, especially enteric coated tablets or capsules. In this regard, compositions are especially preferred which contain the Li($C_{18-22}$ PUFA) salt together with sources of one, some or all of the vitamins and the other essential elements, for example selected from vitamins A, $B_1$, $B_2$, $B_3$, $B_6$, $B_{12}$, C, D and E and calcium, copper, zinc, manganese and iron. In another embodiment, the Li($C_{18-22}$ PUFA) salt may be incorporated into an enteral alimentation solution. The nutritional supplement may however contain the Li($C_{18-22}$ PUFA) salt as the sole active ingredient.

For topical administration, the nutritional supplement will again preferably be in a form adapted for regular application in substantially similar quantities and thus the Li($C_{18-22}$ PUFA) salt may particularly conveniently be incorporated within cosmetics, such as facial creams and ointments and the like.

The lithium content in the nutritional supplement will be selected according to the nature of the supplement and its administration route but in general will be within the range 1 ppb to 30% by weight of lithium, preferably 1 ppm to 20% lithium, especially preferably 0.001 to 10% lithium and particularly preferably up to 1% lithium. Obviously, where the nutritional supplement is in the form of a complete foodstuff, the lithium content will be towards the lower ends of the ranges specified above, for example it may conveniently be in the range 1 ppb to 10 ppm, preferably 10 ppb to 1 ppm. Thus, for example in complete foods which might be administered in a dose of 500 g/day, a lithium content of 5 mg might be contemplated. Wore particularly, the daily dosage will generally be such that the adult body receives from 1 microgram to 50 mg, preferably 1 to 10 mg, of lithium per day, and it will preferably be such as to maintain the lithium plasma level above 0.04 mM/l.

In one particularly preferred embodiment therefore the pharmaceutical composition of the invention takes the form of a nutritional supplement comprising a foodstuffs base with included therein, preferably provided with a gastric juice resistant release delaying coating, a Li($C_{18-22}$ PUFA) in a concentration such that said supplement contains from 1 ppb to 1% by weight of lithium. Nutritional supplements prepared from sterilized or deionized base materials would be particularly preferred.

In another preferred embodiment the nutritional supplement comprises a sterile composition containing a Li($C_{18-22}$ PUFA) salt, preferably provide with a gastric juice resistant release delaying coating, together with four or more, preferably eight or more, vitamins or minerals, for example essential vitamins or minerals selected from the group consisting of vitamins A, $B_1$, $B_2$, $B_3$, $B_6$, $B_{12}$, C, D and E and physiologically tolerable calcium, copper, zinc, manganese and iron compounds.

Such nutritional supplements may be used to combat a wide range of conditions associated with essential chemical deficiency, in particular conditions which appear to be associated with immune system malfunction and especially conditions such as combination skin, atopic eczema, psoriasis, seborrheic dermatitis, candidiasis, pityriasis, skin fungal infections and conditions associated with alcoholism, and the uses and methods of the invention are deemed to relate to the treatment of such conditions as well as the conditions mentioned earlier herein.

The compositions of the invention may of course contain further ingredients, such as for example conventional pharmaceutical or topical disinfectant formulation aids, e.g. emulsifiers, extenders, flavours, colouring agents, surfactants, pH adjusting agents, ointment bases, gelling agents, propellants, stabilizers and the like. The compositions may also contain other physiologically active agents.

The present invention will now be illustrated further by the following non-limiting Examples in which all percentages, ratios and parts are by weight unless otherwise specified:

Example 1

Orally Administrable Capsules

Appropriately sized hard or soft gelatin capsules are each filled with 250, 500 or 1000 mg of lithium gamma-linolenate and optionally are provided with an enteric coating.

Alternatively, lithium eicosapentaenoate, lithium arachidonate, or lithium dihomo-gamma-linolenate may be used in place of the lithium gamma-linolenate or a combination of two or more of these four lithium salts may be used.

Example 2

Orally Administrable Capsules

Appropriately sized hard or soft gelatin capsules are each filled with 100 mg of lithium eicosapentaenoate and 400 mg of gamma-linolenyl alcohol and optionally are provided with an enteric coating.

Example 3

Orally Administrable Capsules

Appropriately sized hard or soft gelatin capsules are each filled with 50 mg of lithium arachidonate and 250 mg of dihomo-gamma-linolenyl alcohol and optionally are provided with an enteric coating.

Example 4

Orally Administrable Capsules

Appropriately sized hard or soft gelatin capsules are each filled with 50 mg of lithium eicosapentaenoate, 50 mg of lithium arachidonate and 400 mg of gamma-linolenyl alcohol and optionally are provided with an enteric coating.

Example 5

Orally Administrable Capsules

Appropriately sized hard or soft gelatin capsules are each filled with 50 mg of lithium gamma-linolenate, 50 mg of eicosapentaenyl alcohol and 100 mg of dihomo-gamma linolenic acid and optionally are provided with an enteric coating.

Example 6

Orally Administrable Capsules

Appropriately sized hard or soft gelatin capsules are each filled with 50 mg of lithium arachidonate, 50 mg of docosahexaenyl alcohol (22:6n-3) and 220 mg of evening primrose oil-derived triglycerides and optionally provided with an enteric coating.

Example 7

Parenterally Administrable Solutions

A solution is prepared by dissolving 5 g of lithium gamma-linolenate, alone or with 5 g of lithium arachidonate, lithium eicosapentaenoate, or lithium docosahexaenoate, in 500 ml of saline or glucose solution for intravenous administration. The Li($C_{18-22}$PUFA) salt(s) may be conveniently prepared in glass vials each containing 5 g of the salt which can then be dissolved in sterile water and added to the intravenous solution. Compositions containing the Same lithium salt(s) can be prepared for intramuscular or subcutaneous injection.

Example 8

Solutions for Enteral or Rectal Administration

A solution is prepared by dissolving 5 g of lithium gamma-linolenate (or another Li($C_{18-22}$ PUFA) or a combination of Li($C_{18-22}$PUFA) s) in 100 ml of an enteral or rectal administration solution.

Example 9

Parenterally Administrable Emulsions

An emulsion is prepared by emulsifying one volume of an oil phase comprising 5 g of lithium eicosapentaenoate and 5 g of lithium gamma-linolenate dissolved in 100 g of corn oil with ten volumes of an aqueous phase comprising a 1% lecithin and 2% glycerol aqueous solution.

Example 10

Parenterally Administrable Emulsions

An emulsion is prepared by emulsifying one volume of an oil phase comprising 10 g of lithium dihomo-gamma-linolenate and 5 g of eicosapentaenyl alcohol dissolved in 100 g of corn oil with seven volumes of an aqueous phase comprising a 1.5% lecithin and 2% glycerol aqueous solution.

The eicosapentaenyl alcohol may if desired be replaced by gamma-linolenyl alcohol or any of the other alcohol analogues of the $C_{18-22}$ PUFAs. Similarly other $Li(C_{18-22}$ PUFA) salts may be used in place of lithium dihomo-gamma-linolenate.

Example 11

Orally Administrable Tablets

Tablets are prepared in a conventional manner from lithium gamma-linolenate, arachidonate, eicosapentaenoate or any other $Li(C_{18-22}$ PUFA) admixed with a physiologically acceptable tabletting aid. The mixture is compressed to yield tablets each containing 500 mg of the lithium salt. These tablets may then if desired be provided with a gastric juice resistant enteric coating.

Example 12

Cosmetic Composition

Cosmetic compositions, e.g. creams, lotions or the like, may be prepared by mixing into a conventional cosmetic composition sufficient lithium gamma-linolenate and lithium eicosapentaenoate to produce a composition containing 3% lithium gamma-linolenate and 1% lithium eicosapentaenoate Where the composition contains no aqueous, alcoholic or lipid solvents, the lithium salts are preferably used in finely divided form.

Example 13

Skin and Hair Care Compositions

Skin and hair care compositions, such as lotions, creams or shampoos, may be prepared by mixing into a conventional skin or hair care composition sufficient lithium gamma-linolenate and lithium eicosapentaenoate to yield a composition containing 5% lithium gamma-linolenate and 3% lithium eicosapentaenoate.

Example 14

Surface Disinfecting Composition

A surface disinfecting composition is prepared by disolving in 100 g of 70% ethanol 1 g of lithium gamma-linolenate and 1 g of eicosapentaenyl alcohol. This composition may be absorbed into cellulosic tissues which may then be packed in air- and liquid-tight plastics-lined foil or paper sachets.

Example 15

Surface Disinfecting Composition

A surface disinfecting composition is prepared by emulsifying a mixture of 0.5% lithium arachidonate in water. The composition may be absorbed into tissues as described in Example 14.

Example 16

Surface Disinfecting Composition

A surface disinfecting composition is prepared by emulsifying one volume of an oil phase comprising 1 g of lithium dihomo-gamma-linolenic acid, 1 g of arachidonyl alcohol and 15 g of corn oil with ten volumes of an aqueous phase comprising a 2.5% lecithin and 2% glycerol aqueous solution.

Example 17

Surface Disinfecting Compositions

A surface disinfecting composition is prepared by dissolving 5 parts of lithium gamma-linolenate and 5 parts of lithium arachidonate in 90 parts of water.

Example 18

Surface Disinfecting Compositions

A surface disinfecting composition is prepared by dissolving 2 parts of lithium eicosapentaenoate and 5 parts of gamma-linolenyl alcohol in 93 parts of water or of 70% ethanol.

Example 19

Foodstuffs Composition

A breakfast cereal, for use as a nutritional supplement, contains the following ingredients in each 30 g serving:

| | |
|---|---|
| Vitamin A | 4000 iU |
| Vitamin $B_1$ | 1 mg |
| Vitamin $B_2$ | 1 mg |
| Vitamin C | 50 mg |
| Vitamin D | 400 iU |
| Calcium carbonate | 5 mg |
| Lithium eicosapentaenoate | 20 mg |
| Rolled oats ad | 30 g |

Example 20

Multi-Vitamin/Mineral Tablet

Multi-vitamin/mineral tablets for daily ingestion each contain the following ingredients:

| | |
|---|---|
| Vitamin A | 4000 iU |
| Vitamin $B_1$ | 1.5 mg |
| Vitamin $B_2$ | 1 mg |
| Vitamin $B_6$ | 1 mg |
| Vitamin $B_3$ | 2 mg |
| Vitamin C | 40 mg |
| Vitamin D | 400 iU |
| Vitamin E | 4 mg |
| Calcium carbonate | 5 mg |
| Lithium gammalinolenate | 50 mg |
| Iron (II) carbonate | 10 mg |
| Manganese sulphate | 1 mg |
| Nicotinamide | 15 mg |
| Tableting base ad | 450 mg |

The tablet components are mixed and compressed to form biconvex tablets which are then coated in a conventional manner. If desired the lithium gamma-linolenate may be precoated with a gastric juice resistant release delaying coating (e.g. a Eudragit coating) or it may be incorporated into a matrix of such a coating material, ground to a powder and then incorporated into the multi-vitamin/mineral tablet.

Example 21

Cosmetic Composition

A night cleansing composition is formed by mixing three parts by weight of lithium gamma-linolenate with ninety seven parts by weight of a cosmetic night cleansing cream base.

Example 22

Body Lotion

A body lotion is formed by mixing 3 Darts by weight of lithium gammalinolenate with 96 parts by weight of a body lotion base.

Example 23

Face Cream

A day face cream is formed by mixing 4 parts by weight of lithium gammalinolenate with 96 Darts by weight of a face cream base.

Example 24

Complete Foodstuff

A complete foodstuff, particularly suited for administration to geriatric or convalescent subjects at a daily dosage of about 500 g/day, is prepared by admixing 70 mg of lithium gammalinolenate together with 500 g of a complete foodstuffs composition containing all other major essential nutrients.

Example 25

Parenteral Nutrition Solution

A solution for parenteral nutrition is prepared by dissolving 1 g of lithium linoleate in 500 ml of an aqueous parenteral nutrition solution. The aqueous nutrition solution used may for example be Vamin N or Vamin Glucose, optionally admixed about 13:1 by volume with Ped-El.

Example 26

Parenteral Nutrition Solution

A solution is prepared analogously to Example 25 but incorporating 1 g of lithium linoleate and 0.3 g of lithium alpha-linolenate in place of the 1 g of lithium linoleate.

Example 27

Parenteral Nutrition Solution

A solution is prepared analogously to Example 25 but incorporating 1 g of lithium linoleate, 0.3 g of lithium alpha-linolenate, 0.3 g of lithium gamma-linolenate and 0.3 g of lithium eicosapentaenoate in place of the 1g of lithium linoleate.

Example 28

Injection Solutions for Addition to Parenteral Nutrition Fluids

Solutions are prepared containing:

| | | |
|---|---|---|
| (a) lithium linoleate | 1 | g |
| ethanol/0.9% saline (50/50 by volume) | 10 | ml |
| (b) lithium linoleate | 1 | g |
| lithium alpha-linolenate | 0.3 | g |
| ethanol/0.9% saline (50/50 by volume) | 10 | ml |
| (c) lithium linoleate | 1 | g |
| lithium alpha-linolenate | 0.3 | g |
| lithium gamma-linolenate | 0.3 | g |
| lithium eicosapentaenoate | 0.3 | g |
| ethanol/0.9% saline (50/50 by volume) | 10 | ml |

These solutions are each filled into vials under aseptic conditions and sealed therein. The contents of such vials may be added to 100 ml or 500 ml or other sizes of bottles of aqueous fluids for parenteral nutrition which do not already contain essential fatty acid In this Example, in place of the $Li(C_{18-22} PUFA)$ salts specified other lithium salts may instead be used, for example salts of n-6 PUFAs such as lithium dihomogamma linolenate, lithium arachidonate, lithium adrenate and lithium docosapentaenoate(22:5n-6) and salts of the n-3 PUFAs such as lithium stearidonate, lithium 20:4n-3, lithium docosapentaenoate (22:5n-3) and lithium docosahexaenoate (22:6n-3).

Example 29

Parenteral Solutions 5 g of lithium gamma-linolenate or lithium eicosapentaenoate (or another $Li(C_{18-22}$ PUFA salt) is dissolved in 500 ml of physiological saline containing 5% glucose and the solution is filled into bottles, flasks or bags under aseptic conditions. Such containers may then be used for parenteral administration, e.g. by infusion, of the $Li(C_{18-22}$ PUFA).

Example 30

Injection Solutions 3 g of lithium gamma-linolenate (or another $Li(C_{18-22}$ PUFA) salt is dissolved in 10 ml of an ethanol/0.9% saline (50/50 by volume) mixture. The solution is filled into a vial under sterile conditions. The solution may be used for administration of the $Li(C_{18-22}$ PUFA) salt in the treatment of disease.

Example 31

Solubility

The change in lithium and PUFA solubilities conferred by formation of the $Li(C_{18-22}$ PUFA) salts is illustrated by the following experiments.

(A) Equimolar amounts of lithium gamma-linolenate (500 mg) and lithium chloride (128.4 mg) were dissolved in 50 ml distilled water. Each 50 ml water contained 11.4 mg lithium. Each aqueous solution was then shaken with 250 ml of chloroform/methanol (2/1 by volume). The chloroform/methanol fraction was then separated off and evaporated to dryness under a stream of nitrogen. The mass of dry extract from the chloroform/methanol phase was weighed and its lithium content determined by flame photometry. The lithium content of the aqueous phase was also measured by flame photometry.

(B) 1 g of pure gamma-linolenic acid was dissolved in 10 ml of chloroform/methanol (2/1 by volume). The resulting solution was then thoroughly shaken with 50 ml distilled water. The chloroform/methanol phase was then separated off and evaporated to dryness in a stream of nitrogen and the mass of dry extract was weighed.

The experiments were repeated five times and the ranges of results obtained are shown in the following tables:

TABLE I

| | Percentage of total lithium in: | |
|---|---|---|
| | Aqueous phase | Chloroform/methanol phase |
| Lithium chloride | 95-91% | 1-5% |
| Lithium gammalinolenate | 11-17% | 83-89% |

TABLE II

| | Percentage of total fatty acid/ fatty acid salt* in: | |
|---|---|---|
| | Aqueous phase | Chloroform/ methanol phase |
| Gamma-linolenic acid | 2-9% | 91-98% |
| Lithium gammalinolenate | 11-17% | 83-89% |

(*taken as equivalent to the percenatge of lithium)

These results clearly show that lithium in the form of the gamma-linolenate salt and gamma-linolenic acid as the lithium salt move readily between the aqueous and the lipophilic phases whereas lithium as the chloride salt and gamma-linolenic acid as the free acid do not.

I claim:

1. A method of treatment of the human or animal body to combat conditions responsive to lithium and/or $C_{18-22}$ polyunsaturated fatty acid therapy that is a method of parenteral nutrition or of treatment to combat a condition selected from the group consisting of: essential fatty acid deficiency and conditions associated therewith; inflammatory and immunological disorders; manic-depressive psychosis, schizophrenia, tardive dyskinesia and depression; disorders associated with smooth muscle spasm; diabetes and complications associated therewith; cancers; alcoholism; combination skin; and cardiovascular disorders, comprising administering to the body an effective amount of a lithium salt of a $C_{18-22}$ polyunsaturated fatty acid, with the proviso that where the lithium salt is administered orally in solid form into the stomach in the treatment of Alzheimer's disease it is administered in a pharmaceutical composition in which it is provided with a gastric juice resistant release delaying coating.

2. A method of combatting transfer of lipid-enveloped viruses between humans or animals or between cells within a human or animal body, which method comprises the surface application or the administration to a said body of a virucidal composition comprising a lithium salt of a $C_{18-22}$ polyunsaturated fatty acid.

3. A method as claimed in claim 2 for inhibiting transmission of sexually transmited diseases which method comprises applying a said virucidal composition to inanimate or external body surfaces susceptible to contact with body fluids.

4. A method of treatment of the human or animal body to combat conditions associated with essential lithium deficiency, said method comprising the steps of determining that the lithium plasma level of said body is depressed relative to that of a healthy subject, and administering to said body a nutritional supplement comprising a physiologically tolerable lithium salt of a $C_{18-22}$ polyunsaturated fatty acid with the proviso that where said lithium salt is administered orally in solid form into the stomach in the treatment of Alzheimer's disease it is administered in a pharmaceutical composition in which it is provided with a gastric juice resistant release delaying coating.

5. A method as claimed in claim 4 wherein said nutritional supplement is in the form of a parenteral or enteral alimentation solution.

6. A method as claimed in claim 4 wherein said nutritional supplement is in the form of an orally administrable composition.

7. A method as claimed in claim 6 wherein the lithium salt of said nutritional supplement is provided with a gastric juice resistant release delaying coating.

8. A method as claimed in claim 6 wherein said nutritional supplement is in the form of a complete foodstuff.

9. A method as claimed in claim 5 wherein said nutritional supplement is in the form of an enteral alimentation solution.

10. A method as claimed in claim 1, wherein said condition is fatty acid deficiency or a condition associated therewith.

11. A method as claimed in claim 1, wherein said condition is selected from the group consisting of inflammatory and immunological disorders.

12. A method as claimed in claim 1, wherein said condition is selected from the group consisting of manic-depressive psychosis, schizophrenia, tardive dyskinesia and depression.

13. A method as claimed in claim 1, wherein said condition is a disorder associated with smooth muscle spasm.

14. A method as claimed in claim 1, wherein said condition is diabetes or a complication associated therewith.

15. A method as claimed in claim 1, wherein said condition is a cardiovascular disorder.

* * * * *